United States Patent [19]

Schneider

[11] 4,145,061
[45] Mar. 20, 1979

[54] CLAMPING DEVICE FOR A DENTAL TOOL

[76] Inventor: Hans K. Schneider, Ebrach 209, Ebrach, Fed. Rep. of Germany, 8091

[21] Appl. No.: 840,894

[22] Filed: Oct. 11, 1977

[30] Foreign Application Priority Data

Nov. 6, 1976 [DE] Fed. Rep. of Germany ....... 2650864

[51] Int. Cl.² .......................... B23B 5/22; B23B 5/34; B23B 31/10
[52] U.S. Cl. .......................................... 279/96; 279/6; 279/102
[58] Field of Search ................... 279/102, 96, 71, 9 R, 279/6

[56] References Cited

U.S. PATENT DOCUMENTS 2,920,894  1/1960  Kreinick ............................... 279/6 X

*Primary Examiner*—Travis S. McGehee
*Attorney, Agent, or Firm*—Hans Berman; Hans Berman

[57] ABSTRACT

A clamping device for a dental tool consists of a tubular body whose bore has two coaxially cylindrical, terminal portions and a reduced, slightly eccentric, cylindrical, central portion. A clamping sleeve is conformingly rotatable in one of the terminal portions. Its slightly eccentric bore is of uniform cross section equal to that of the central portion of the body. The sleeve can be turned in the body between a position in which the bore of the sleeve and the central bore portion of the body member are aligned for insertion of a dental tool, and another position in which they clamp the tool.

12 Claims, 3 Drawing Figures

CLAMPING DEVICE FOR A DENTAL TOOL

This invention relates to clamps, and particularly to a device for clamping an elongated tool.

The clamping device of the invention will be described hereinbelow with reference to a dental tool holder for a root canal tool, but other applications will readily suggest themselves. The needle or other tool employed for cleaning the root canal of a tooth must penetrate to the very bottom of the canal, but must not penetrate the bottom. It has been proposed to slip a rubber ring over the needle as an abutment which engages an outer surface of the tooth and thereby limits the depth of needle insertion. The rubber ring is compressible and does not hold the needle in a precisely defined end position. Moreover, the working end of many root canal tools is enlarged and makes it difficult to slip the ring over the needle shaft. Other proposed abutments share at least some of the disadvantages of the rubber ring and are relatively difficult to handle.

The primary object of this invention is the provision of a clamping device which is attached to a root canal tool in a simple manner, yet precisely defines the available depth of tool insertion in a root canal.

With this object and other in view, the clamping device of the invention includes a body member and a sleeve member secured to each other for angular movement about an axis between two relative positions. Respective portions of bores in the two members constitute parts of a continuous, elongated receptacle in each of the two positions. In one position, the bore portions are aligned. In the other position, they are offset transversely of the direction of receptacle elongation.

Other features, additional objects, and many of the attendant advantages of this invention will readily be appreciated as the same becomes better understood by reference to the appended drawing in which.

Figure 1:
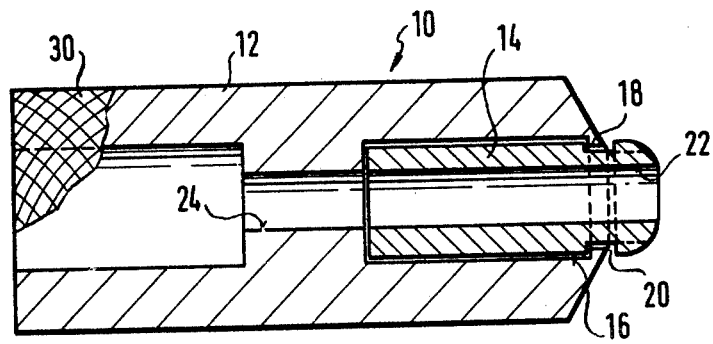
FIG. 1 shows a clamping device of the invention in enlarged side elevation and mostly in section on the line I—I in FIG. 2.

The clamping device 10 consists of a cylindrical body 12 and of a cylindrical sleeve 14 conformingly received in an axially terminal portion of a bore 16 of the body 12 for angular movement about the common axis of the body 12 and sleeve 14 which is also the axis of the two cylindrical, terminal portions of the bore 16. The sleeve 14 axially projects outward of the bore 16 and is axially secured in the bore 16 by a radial flange 18 projecting from the body 12 into an annular, circumferential groove 20 of the sleeve 14.

Figure 3:
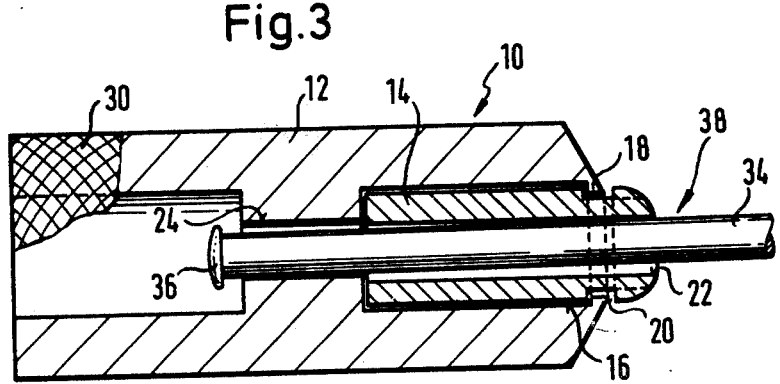
FIG. 3 illustrates the clamping device in another position of its parts in a view corresponding to that of FIG. 1.

The bore 22 of the sleeve 14 is cylindrical about an axis parallel to, but slightly offset from the afore-mentioned common axis. The reduced central portion 24 of the bore 16 is equal in cross section to the bore 22 and equally eccentric so that the bore 22 and the bore portion 24 may be aligned to form respective sections of a continuous receptacle of uniform cross section in the angular position of the sleeve 14 illustrated in FIG. 1. When the sleeve 14 is turned 180° in the bore 16 from the position of FIG. 1 into that of FIG. 3, the receptacle is still of uniform cross section and continuous, but its two sections 22, 24 and transversely offset. Turning of the sleeve 14 in the bore 16 is facilitated by knurls 30 in the outer, cylindrical surface of the body 12 and by two opposite flats 32 or other non-circular configuration on the projecting part of the sleeve 14 which are parallel to the axis of angular sleeve movement and to each other and are conveniently gripped by a small wrench.

Figure 2:
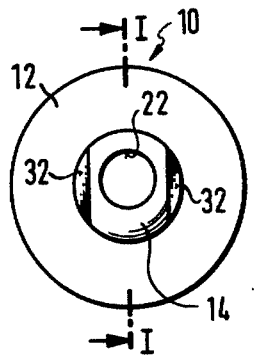
FIG. 2 shows the device of FIG. 1 in front elevation.

When the bores 22, 24 are in the aligned position of FIG. 1, the shaft 34 of a root canal tool is readily introduced from the wide end of the bore 16 remote from the sleeve 14, and the effective cross section of the combined boes 22, 24 is sufficient to pass the enlarged working head of the tool, not itself shown in the drawing. The freely projecting end of the tool is readily set to the desired length. A head 36 on the other end of the shaft 34 prevents the tool from slipping too far out of the clamping device. The shaft 34 thereafter is clamped between the body 12 and the sleeve 14 by turning the body and sleeve relative to each other about the common axis into the position shown in FIG. 2 in which the effective cross section of the receptacle is reduced.

Prior to assembly of the clamping device, the portion of the bore 16 receiving the sleeve 14 has smooth, cylindrical walls. After insertion of the sleeve, the rim of the body 12 about the orifice of the bore 16 is beaded into the groove 20 of the sleeve 14 to constitute the radial flange 18.

While tool shafts varying somewhat in diameter may be secured in the same clamping device of the invention and merely require different angular clamping movement of the body 12 and sleeve 14, it is preferred that the difference between the outer diameter of the tool shaft and the inner diameter of the bores 22, 24 be small enough so that friction will hold the body and sleeve in the angular clamping position. The materials of construction chosen for the body 12, the sleeve 14, and the shaft 34 will thus affect the versatility of the clamping device to some extent in a predictable manner.

During its intended use, the body 14 provides a handle for the root canal tool, and the radial end face of the sleeve 14 limits the depth of insertion of the tool by abuttingly engaging a tooth surface when the tool reaches its innermost position in the root canal. if so desired, the body 14 is attached to the flexible shaft of an electric motor or other prime mover in a conventional manner, not directly relevant to this invention.

It should be understood, of course, that the foregoing disclosure relates only to a preferred embodiment of the invention, and that it is intended to cover all changes and modifications of the example of the invention herein chosen for the purpose of the disclosure which do not constitute departure from the spirit and scope of the invention set forth in the appended claims.

What is claimed is:

1. A clamping device comprising
   (a) an elongated body member formed with a first, longitudinal bore; and
   (b) an elongated tubular sleeve member formed with a second bore therethrough,
      (1) said sleeve member being secured in said first bore for angular movement about an axis between two relative positions,
      (2) respective portions of said bores constituting axially consecutive parts of a continuous receptacle in each of said positions,
      (3) said portions of said bores being substantially aligned in one of said positions and offset transversely of said axis in the other position,
      (4) said sleeve member projecting axially from said first bore, the projecting part of said sleeve member being of non-circular cross-section at right angles to said axis.

2. A device as set forth in claim 1, wherein said portions of said bores are of circular cross section about respective axes parallel to the axis of said angular movement.

3. A device as set forth in claim 1, wherein said projecting part has two opposite planar faces parallel to each other and to said axis.

4. A device as set forth in claim 1, further comprising securing means axially securing said sleeve member in said first bore.

5. A device as set forth in claim 4, wherein said securing means including an annular radial flange on said body member in said first bore, said sleeve member being formed with an annular, circumferential groove receiving said flange.

6. A device as set forth in claim 1, wherein said body member has an outer cylindrical face parallel to said axis, said outer face being formed with knurls.

7. A device as set forth in claim 1, wherein said first bore has two longitudinally terminal portions connected by an intermediate portion of reduced cross section, one of said terminal portions conformingly receiving said sleeve member for rotation about said axis, said intermediate portion constituting one of said parts of said receptacle.

8. A clamping device comprising:
  (a) an elongated body member formed with a first longitudinal bore and including an annular flange transversely projecting into said bore;
  (b) a tubular sleeve member formed with a second bore therethrough,
    (1) said sleeve member being formed with an annular, cumferential groove receiving said flange, and being longitudinally secured in said first bore by said flange for angular movement about an axis between two relative positions,
    (2) respective portions of said bores constituting axially consecutive parts of a continuous receptacle in each of said positions,
    (3) said portions of said bores being substantially aligned in one of said positions and offset transversely of said axis in the other position.

9. A device as set forth in claim 8, wherein said sleeve member axially projects from said first bore, the projecting part of said sleeve member being of non-circular cross-section at right angles to said axis.

10. A clamping device comprising:
  (a) an elongated body member formed with a first longitudinal bore,
    (1) said bore having two longitudinally open terminal portions connected by an intermediate portion of reduced cross section; and
  (b) a sleeve member formed with a second bore therethrough,
    (1) said sleeve member being received conformingly in one of said terminal portions for angular movement about a longitudinal axis between two positions,
    (2) said second bore and said intermediate portion constituting consecutive parts of a continuous elongated passage in each of said positions,
    (3) said portions of said bore being substantially aligned in one of said positions and offset transversely of said passage in each of said positions.

11. A device as set forth in claim 10, wherein the effective cross section of said passage is reduced by angular movement of said sleeve member from said one position to said second position.

12. A device as set forth in claim 10, wherein said terminal portions are cylindrical about said axis, said intermediate portion being cylindrical about another axis parallel to and transversely offset from the axis of said terminal portions.

* * * * *